United States Patent [19]
Miura et al.

[11] Patent Number: 5,585,916
[45] Date of Patent: Dec. 17, 1996

[54] SURFACE INSPECTING DEVICE

[75] Inventors: Seiya Miura; Michio Kohno, both of Utsunomiya, Japan

[73] Assignee: Canon Kabushiki Kaisha, Tokyo, Japan

[21] Appl. No.: 257,535

[22] Filed: Jun. 9, 1994

[30]  Foreign Application Priority Data

Jun. 15, 1993  [JP]  Japan .................................. 5-143627

[51] Int. Cl.$^6$ ................................................ G01N 21/21
[52] U.S. Cl. .................. 356/237; 250/559.09; 250/559.4
[58] Field of Search ..................................... 356/237, 338, 356/339, 343; 250/572, 559.09, 559.4, 559.41

[56]  References Cited

U.S. PATENT DOCUMENTS

| | | | |
|---|---|---|---|
| 4,669,875 | 6/1987 | Shiba et al. ............................... | 356/237 |
| 4,740,079 | 4/1988 | Koizumi et al. .......................... | 250/572 |
| 4,795,911 | 1/1989 | Kohno et al. ............................. | 250/572 |
| 4,831,274 | 5/1989 | Kohno et al. ............................. | 250/563 |
| 4,886,975 | 12/1989 | Murakami et al. ...................... | 250/572 |
| 4,999,511 | 3/1991 | Kohno ....................................... | 250/572 |
| 5,017,798 | 5/1991 | Murakami et al. ...................... | 250/572 |
| 5,105,092 | 4/1992 | Natsubori et al. ....................... | 250/572 |
| 5,274,434 | 12/1993 | Morioka et al. ......................... | 356/237 |

*Primary Examiner*—K. Hantis
*Attorney, Agent, or Firm*—Fitzpatrick, Cella, Harper & Scinto

[57]  ABSTRACT

A surface inspection device and method wherein an illumination system is arranged so that light from a laser diode is transformed into parallel light which is then directed through a half waveplate to a surface of a reticle to be inspected. A detecting system is arranged so that scattered light from a particle on the surface, for example, is collected by a lens array onto a sensor array. The direction of polarization of the parallel light defined by the half waveplate is made substantially parallel to a plane containing optical axes of the illumination system and the detecting system. Thus, even if an error occurs in the angle of incidence of the parallel light upon the reticle, a change in scattered light intensity due to interference between scattered light is kept small to assure accurate discrimination of the particle.

16 Claims, 15 Drawing Sheets

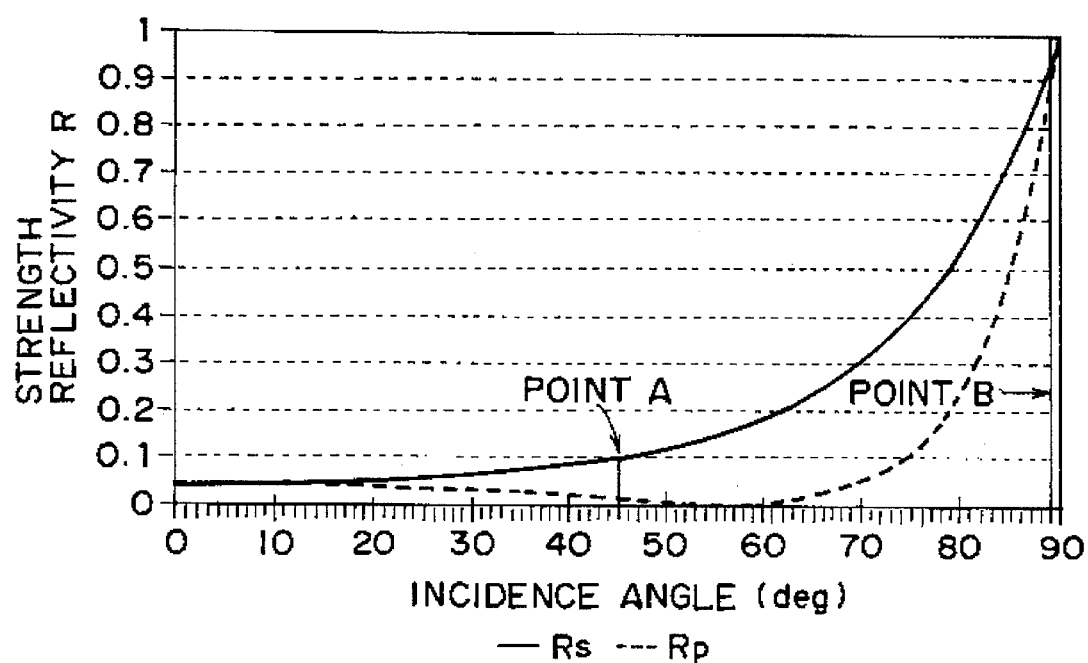
F I G. 5

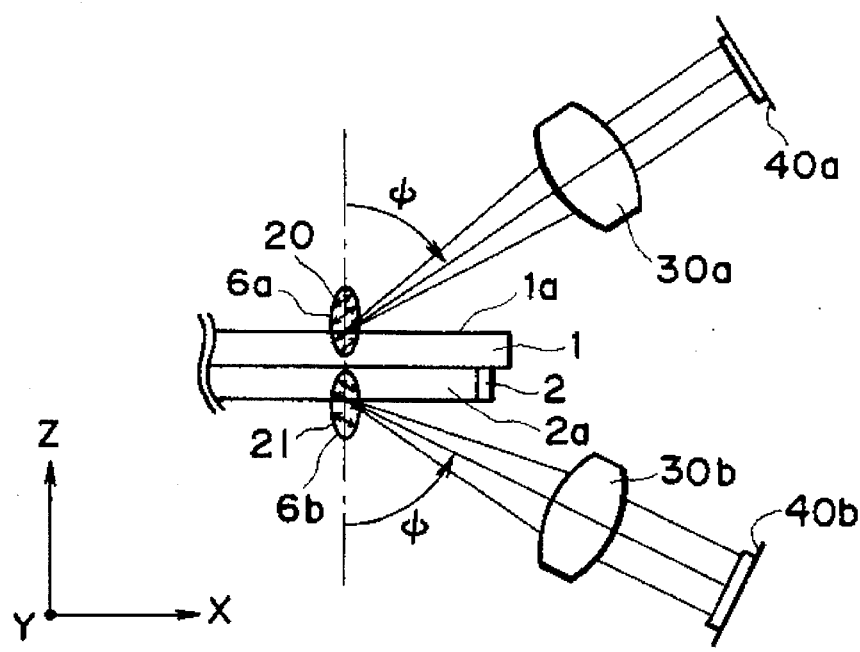
F I G. 13A
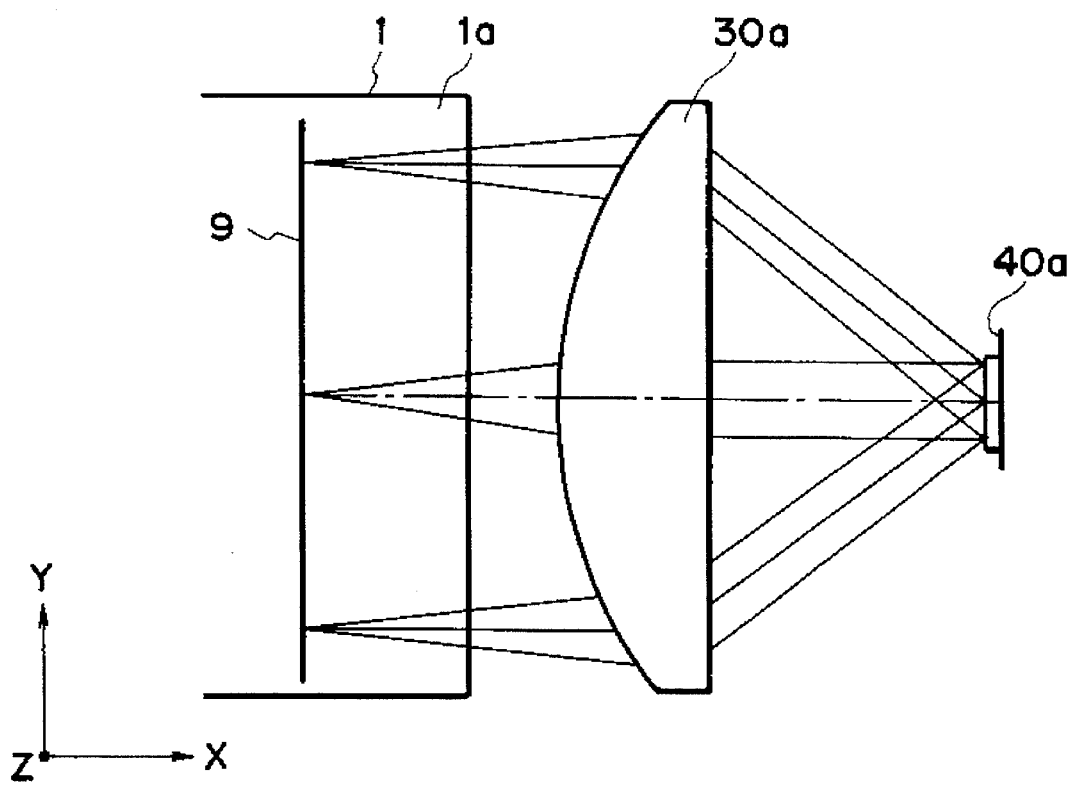
F I G. 13B

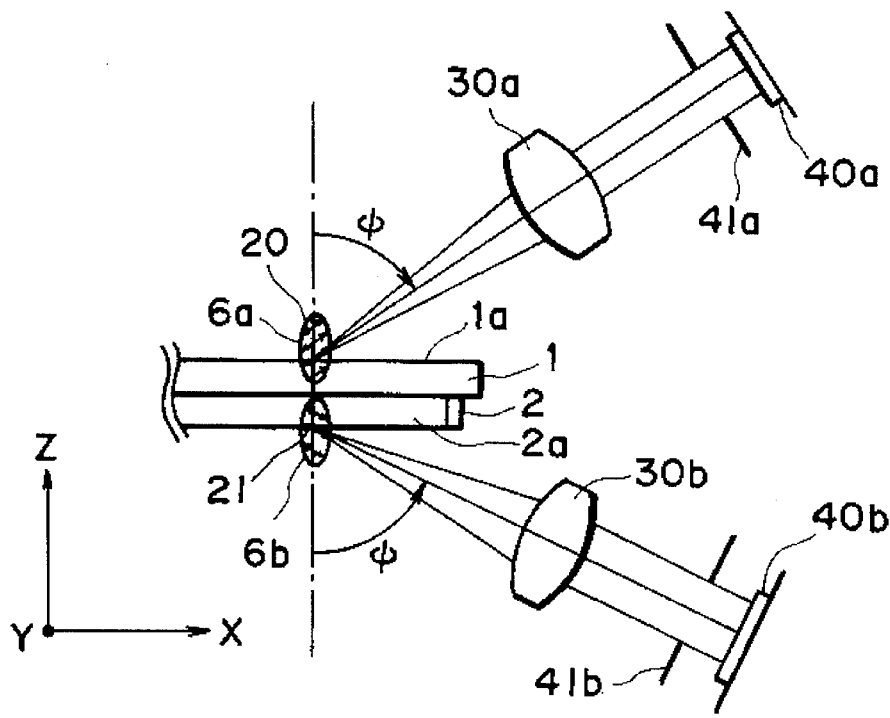
F I G. 14A
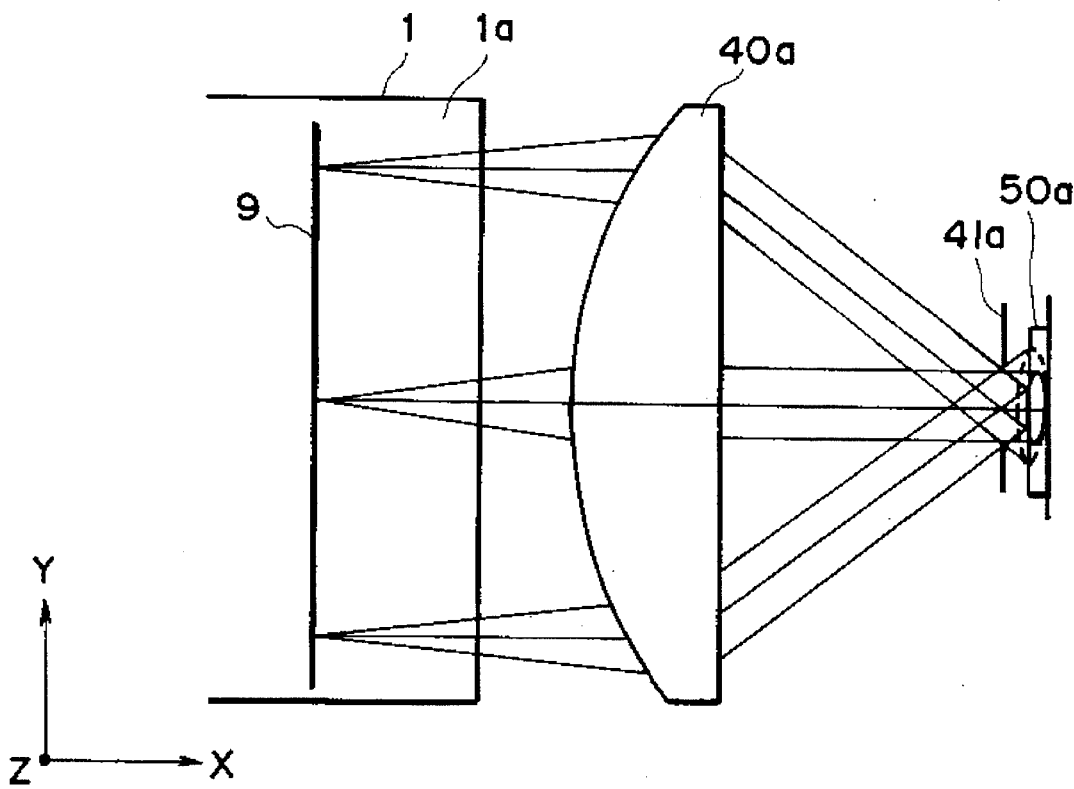
F I G. 14B

SURFACE INSPECTING DEVICE

FIELD OF THE INVENTION AND RELATED ART

This invention relates to a surface inspecting device for inspecting the state of a surface to be examined. More particularly, the invention is concerned with a surface inspecting device suitably usable in a semiconductor device manufacturing apparatus, for example, for detecting with good precision the presence/absence of and the position of, if any, a foreign particle such as non-transmissive dust, for example, adhered to a substrate such as a reticle or photomask, having a circuit pattern, or to a pellicle protection film covering the substrate.

In IC manufacturing processes, generally, a circuit pattern formed on a reticle or photomask is transferred to a resist-coated wafer by using a semiconductor printing apparatus (stepper or mask aligner).

if in this pattern transfer process there is a pattern defect or fault, or a foreign particle such as dust on the surface of the substrate, it is also transferred to the wafer in the pattern transfer process. This apparently degrades the yield of ICs.

Particularly, when a reticle is used and a circuit pattern is printed on a wafer surface through a step-and-repeat process, the presence of only one particle on the reticle surface results in distribution of printed particles all over the wafer surface. This considerably damages the yield of IC manufacturing processes.

Thus, inspection of any foreign particle on a substrate is required in the IC manufacturing processes, and many proposals have been made in this respect. Generally, such a proposal is based on the property that the foreign particle scatters light omnidirectionally or isotropically.

As regards the subject to be inspected, the proposed inspection methods may be classified into two: a method in which the surface of a patterned substrate (pattern bearing surface) is inspected (which may be called a "patterned surface inspection method"), and a method in which a blank surface with no pattern or the surface of a dust-protecting pellicle film attached to the substrate is inspected (which may be called a "blank surface inspection method").

The former, i.e., the patterned surface inspection method, usually employs an optical arrangement by which the substrate is scanned two-dimensionally with an inspecting laser beam of a restricted beam diameter of about 30 microns, and scattered light from a particle of a size of 1–2 microns is selectively received independently of diffraction light caused by the circuit pattern.

The latter, i.e., the blank surface inspection method, uses an inspecting laser beam of a large beam diameter of about 1 mm for inspection of a particle of a size of about 20–30 microns.

Generally, a pellicle surface or a blank surface is projected on the surface of a wafer in a defocused state and, therefore, there is a small possibility that a particle adhered to the pellicle surface or blank surface is transferred to the wafer surface as an image. If, however, the particle size is large, the printing light may be eclipsed by the particle, causing non-uniformness of illuminance and degraded resolving power. Thus, a surface inspection device should have a performance of detecting a particle of about a 20 micron size quickly and with good precision.

There is a method in which a laser beam is projected substantially in parallel so as to illuminate a linear area on the surface of a reticle to be inspected at once, and in which scattered light from a particle, if any, in the linear area is received by a line sensor, while the reticle is moved in a direction perpendicular to the illumination line to accomplish the inspection of the whole surface of the reticle. However, when the laser beam is projected to the reticle exactly parallel to the reticle surface and if the reticle is inclined with respect to the projected laser beam, the whole surface of the reticle is no more illuminated with the light and inspection of the whole reticle surface ends in failure.

Thus, the laser beam might be projected to the reticle surface obliquely. On that occasion, however, there will occur interference between light reflected by the surface of the reticle (substrate) and light directly impinging on the particle and reflected thereby, this causing a change in intensity of scattered light from the particle. Namely, the intensity of scattered light from a larger particle might become lower than that of scattered light from a smaller particle. Thus, it is not possible to detect the size of the particle accurately.

SUMMARY OF THE INVENTION

It is accordingly an object of the present invention to provide an improved surface inspection device by which the magnitude of a particle can be determined accurately.

It is another object of the present invention to provide an exposure apparatus having such an inspection device incorporated thereinto.

It is a further object of the present invention to provide a microdevice manufacturing method including a surface inspection step based on an inspection device such as described above.

In accordance with an aspect of the present invention, there is provided a surface inspection device which comprises illumination means for projecting light to a surface to be inspected, obliquely, and detecting means for detecting scattered light produced by a particle, for example, on the surface being inspected, wherein the illumination means is adapted to project onto the surface inspected a linearly polarized light being polarized in a direction substantially parallel to a plane which contains an optical axis of the illumination means and an optical axis of the detecting means.

In accordance with another aspect of the present invention, there is provided an exposure apparatus which comprises illumination means for projecting light to a surface of a mask to be inspected, obliquely, and detecting means for detecting scattered light produced by a particle, for example, on the surface being inspected, wherein the illumination means is adapted to project onto the surface inspected a linearly polarized light being polarized in a direction substantially parallel to a plane which contains an optical axis of the illumination means and an optical axis of the detecting means.

In accordance with a further aspect of the present invention, there is provided a microdevice manufacturing method for transferring a device pattern of a mask onto a substrate to be exposed, which method comprises projecting light obliquely to the surface of the mask to be inspected, through illumination means; detecting scattered light produced by a particle, for example, on the surface being inspected, through detecting means, to discriminate the appropriateness of using that mask; and exposing a substrate to be exposed, to the device pattern of the mask if the usability of it is determined; wherein the illumination means serves to project onto the surface inspected a linearly polarized light being polarized in a direction substantially parallel to a plane which contains an optical axis of the illumination means and an optical axis of the detecting means.

In one preferred form of the present invention, an angle of 3.5±3 deg. may be set between the optical axis of the illumination means and the surface to be inspected.

Microdevices which can be manufactured by an exposure apparatus or a device manufacturing method according to the present invention may be semiconductor memories, semiconductor microprocessors, magnetic heads, CCDs or liquid crystal panels, for example. In the exposure apparatus or device manufacturing method of the present invention, the appropriateness of using a mask can be discriminated accurately. Therefore, it is possible to increase the yield in device manufacturing processes significantly.

These and other objects, features and advantages of the present invention will become more apparent upon a consideration of the following description of the preferred embodiments of the present invention taken in conjunction with the accompanying drawings.

BRIEF DESCRIPTION OF THE DRAWINGS

FIG. 5 is a graph for explaining the dependence of reflectivity of the surface of a derivative upon the angle of incidence of light.

FIGS. 13A and 13B are schematic illustrations for explaining a fourth embodiment of the present invention, wherein FIG. 13A is a sectional view and FIG. 13B is a plan view.

FIGS. 14A and 14B are schematic illustrations for explaining a fifth embodiment of the present invention, wherein FIG. 14A is a sectional view and FIG. 14B is a plan view.

DESCRIPTION OF THE PREFERRED EMBODIMENTS

Figure 1A:
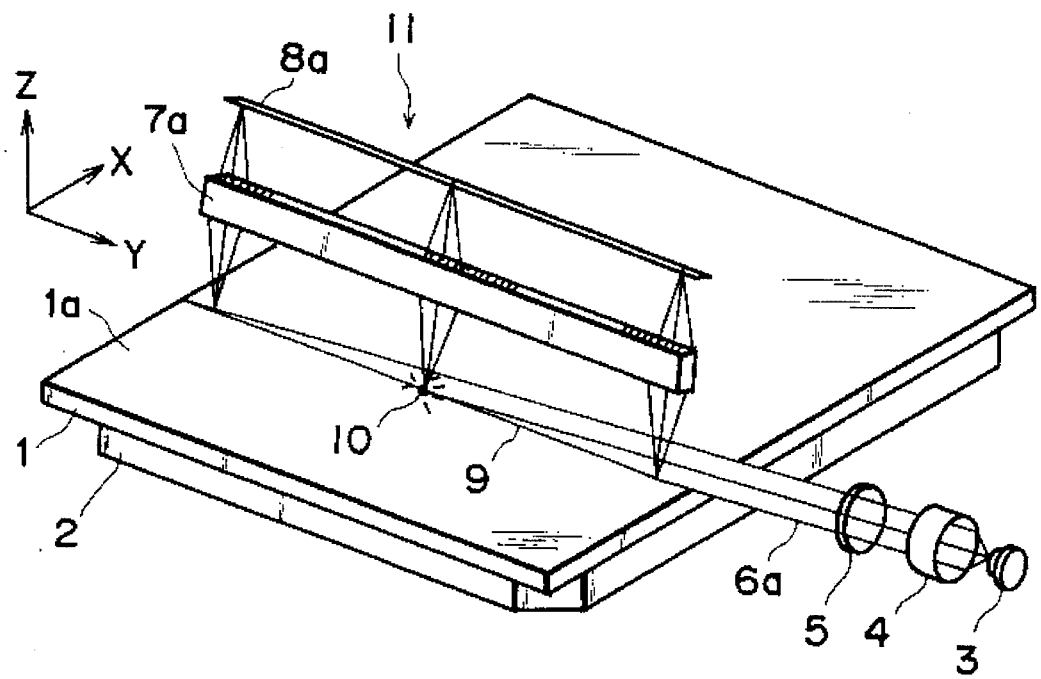
FIGS. 1A and 1B are schematic views for explaining a first embodiment of the present invention.
Figure 1B:
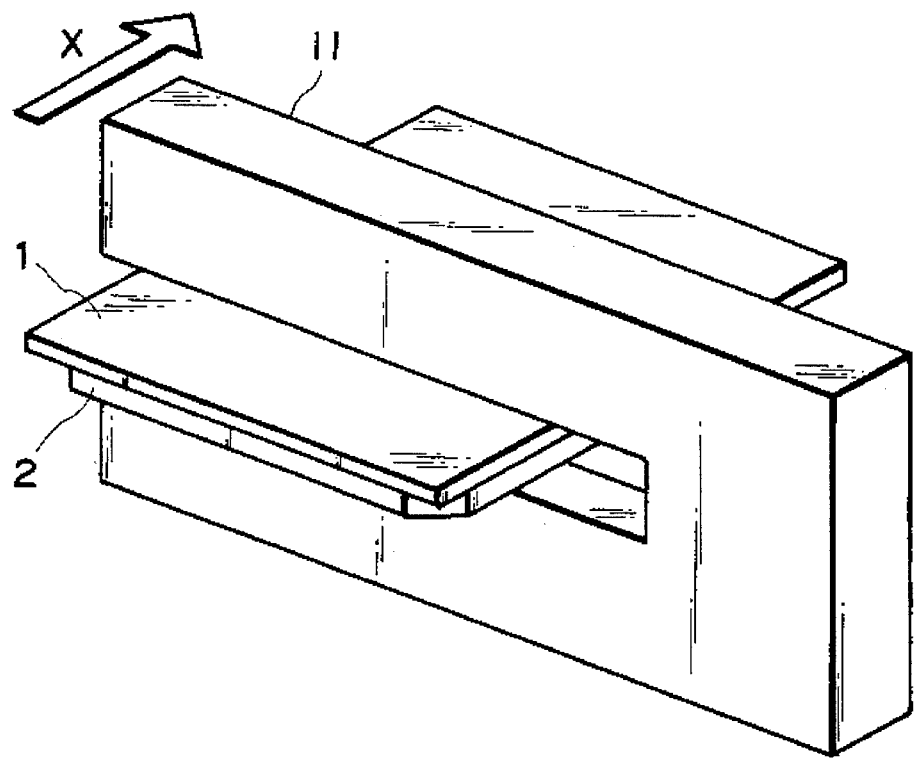

Referring to FIGS. 1A and 1B, a first embodiment of the present invention will be explained.

FIG. 1A shows a basic structure of a surface inspecting device according to the first embodiment. In FIG. 1A, for simplicity in illustration, only a particle inspecting optical system at the back side (blank surface) 1a of a glass substrate 1 of a reticle is illustrated. Actually, the device is provided with an additional particle inspecting optical system for inspection of a pellicle film for protecting the front surface (circuit pattern bearing surface) of the glass substrate of the reticle against any particles. Denoted at 2 in the drawings is a pellicle frame by which the pellicle film is supported.

Semiconductor laser 3 emits a divergent linearly polarized laser beam which is transformed into parallel light by a collimator lens 4. The parallel light 6a is received by a half waveplate 5 disposed along the light path, whereby its axis of linear polarization is set in a predetermined polarization direction. Then, the light is projected on the blank surface 1a obliquely and substantially parallel thereto. By this, a linear illumination region 9 is defined on the blank surface 1a (surface to be inspected) with the laser beam.

If a particle 10 is present on the illumination region 9, the particle produces scattered light. By means of a scattered light receiving imaging lens (lens array) 7a having lens elements disposed along the lengthwise direction of the illumination region 9, the scattered light is collected onto a line sensor 8a. The imaging lens 7a is arranged to image the illumination region 9 upon the line sensor 8a.

As shown in FIG. 1B, the optical system 11 as a whole is scanningly moved rectilinearly along a direction which is perpendicular to the lengthwise direction of the illumination region 9 and which is along the blank surface 1a, that is, in the X direction, whereby inspection of the whole blank surface 1a is accomplished.

Figure 2:
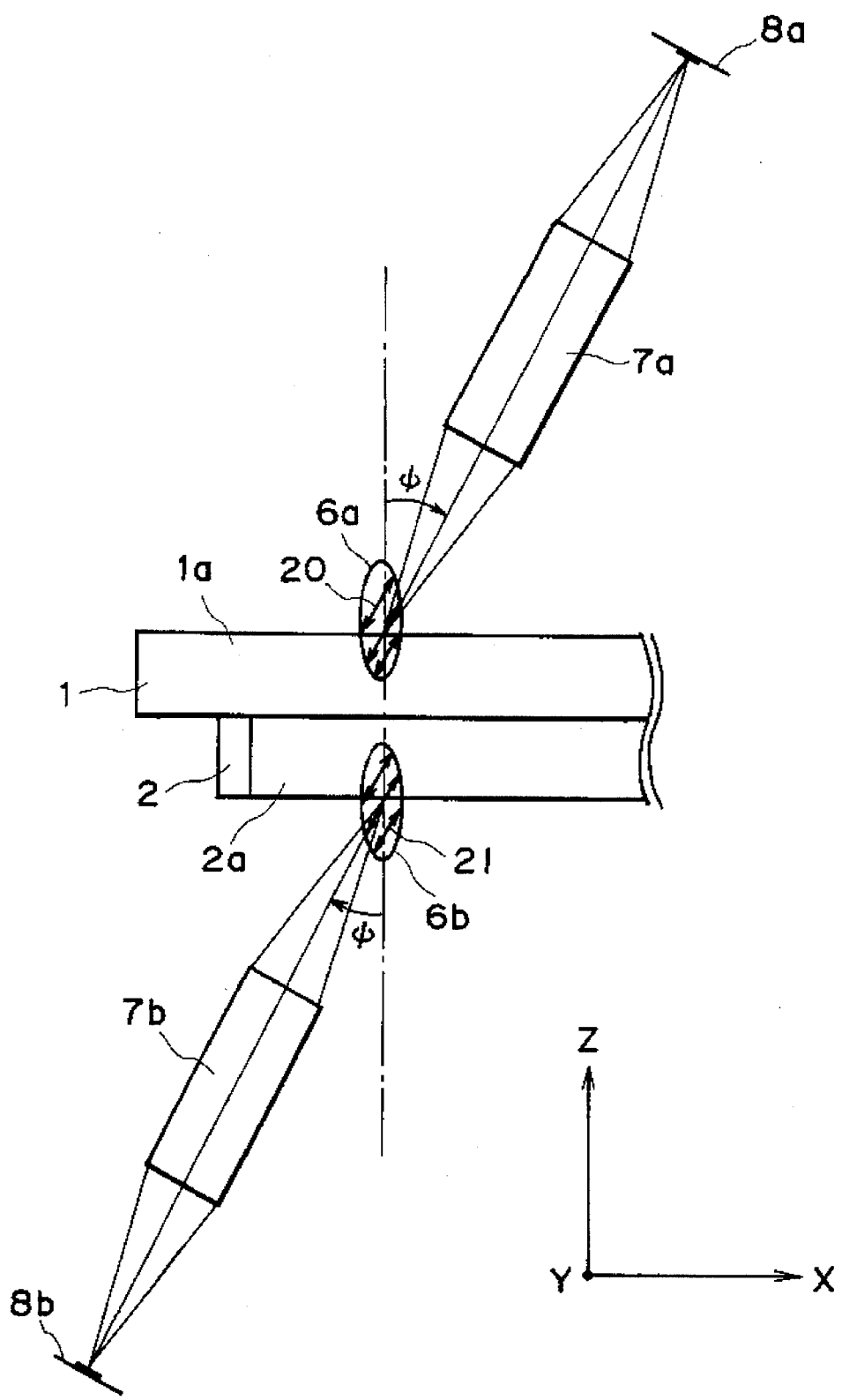
FIG. 2 is a sectional view of the first embodiment of the present invention.

FIG. 2 is a schematic view for explaining the direction of setting the polarization axis of the laser beam. As illustrated in FIG. 2, the optical axis of the light receiving imaging lens 7a is disposed with a tilt ϕ with respect to a normal to the surface to be inspected. In response thereto, the direction (20) of polarization axis of the laser beam 6a is set with a tilt ϕ with respect to the normal to the surface to be inspected. It is to be noted that in FIG. 2 the laser beam 6b, the scattering light receiving imaging lens 7b, and the line sensor 7b are constituent elements of the pellicle film inspecting optical system, and that reference numeral 21 denotes the direction of polarization axis of the laser beam 6b.

Figure 3:
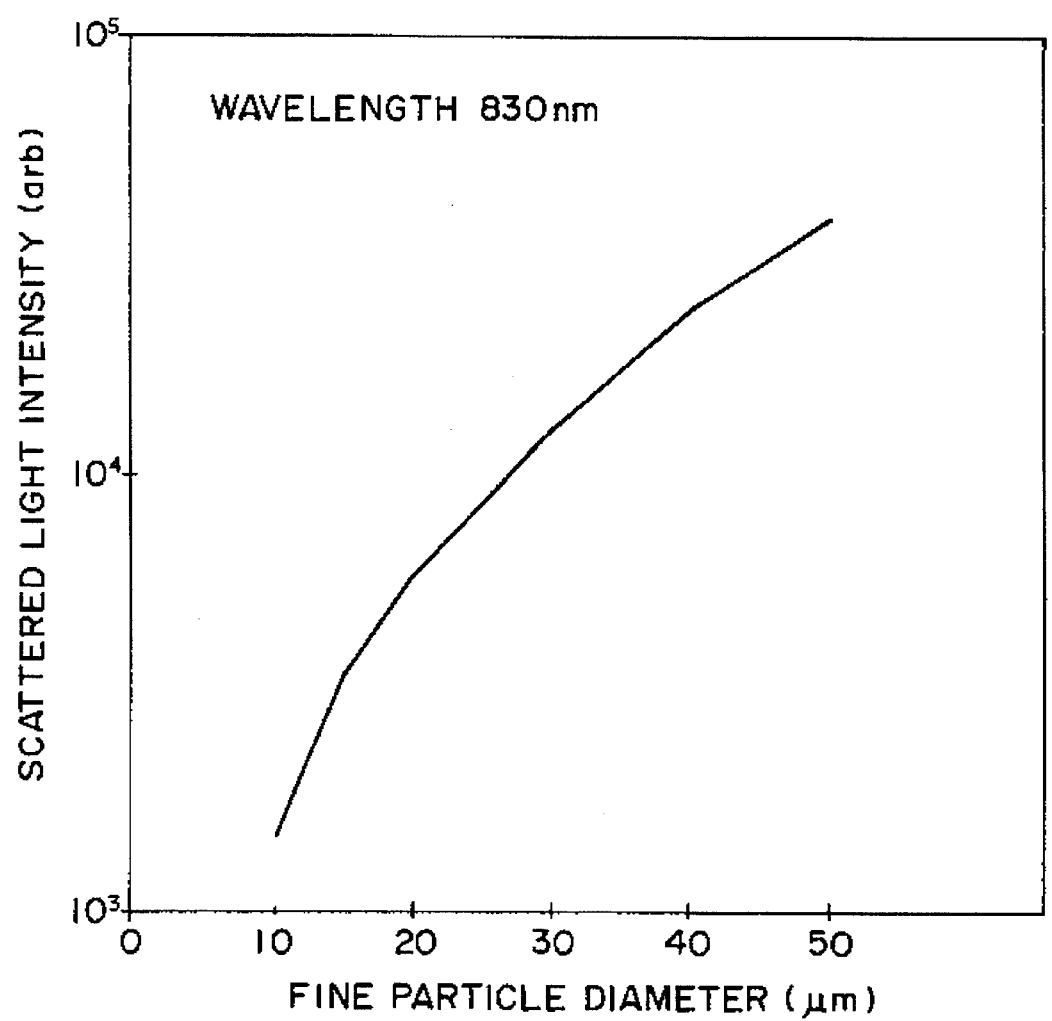
FIG. 3 is a graph for explaining the relation between the diameter of a fine particle and the intensity of scattered light.
Figure 4:
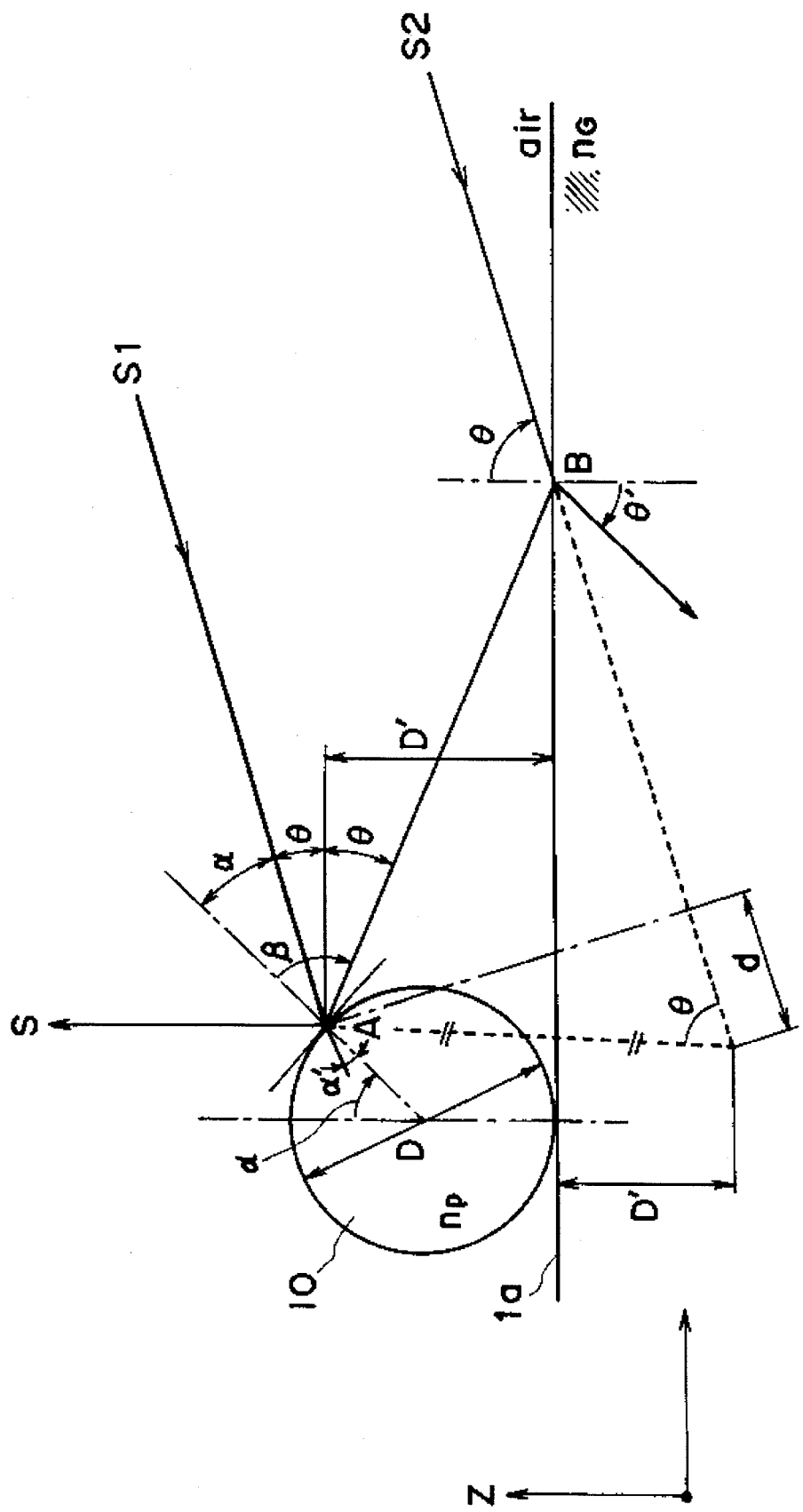
FIG. 4 is a schematic view for explaining interference between scattered lights from the surface being inspected.
Figure 8:
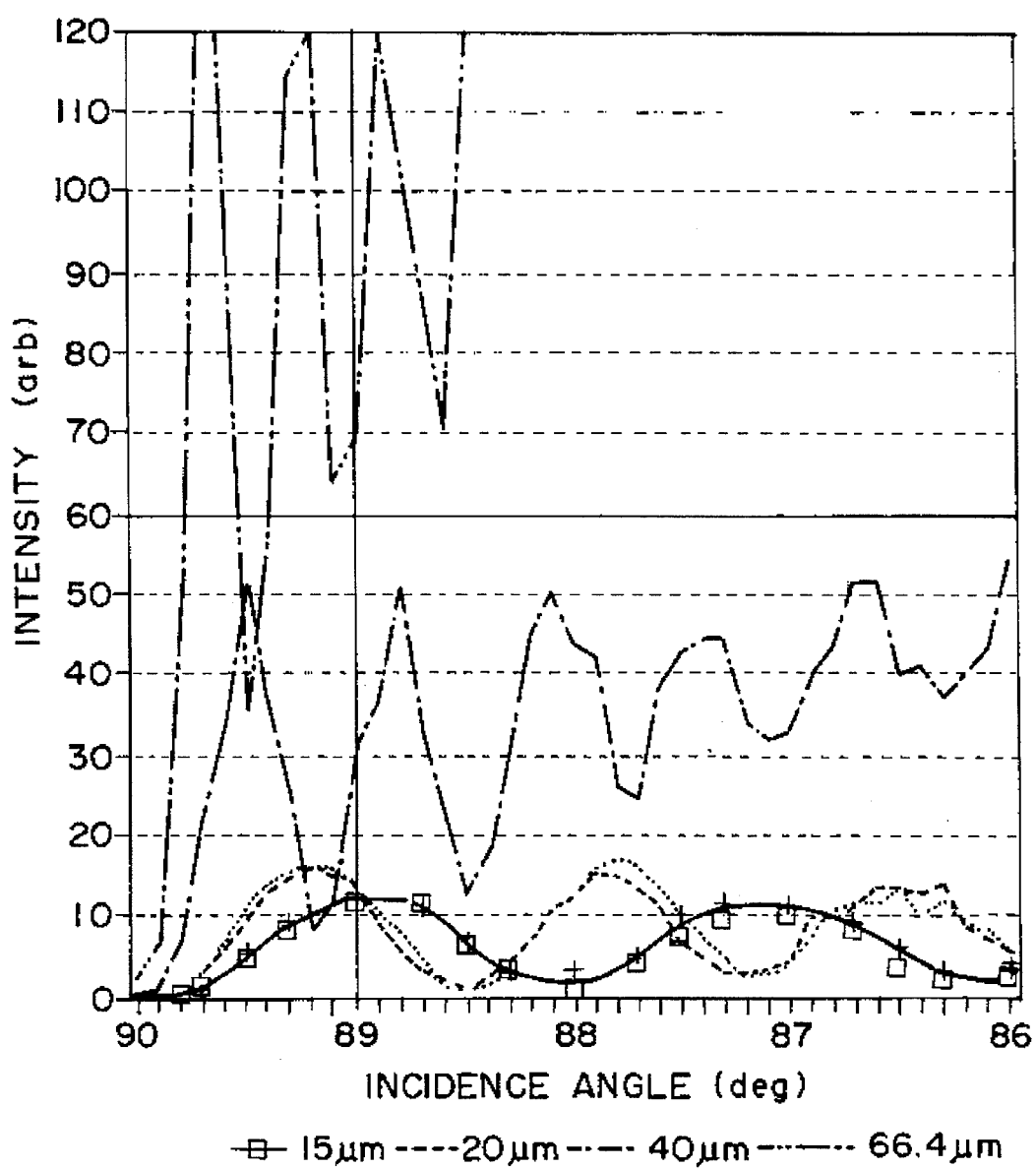
FIG. 8 is a graph wherein changes in intensity of scattered light with a variation in angle of incidence of light are plotted with respect to each of different particle sizes, where S-polarized light is inputted to the surface to be inspected.

As illustrated in FIG. 3, the intensity of scattered light from a particle increases approximately in proportion to the square of the scattering sectional area of the particle. If, however, the light reflected by the glass substrate 1 of the reticle interferes with the light directly impinging on the particle and reflected thereby, then changes in the intensity of scattered light such as shown in FIG. 8 occur. Now, a model shown in FIG. 4 is considered with respect to such a change in intensity of scattered light due to interference. This model is drafted by geometrically and simply illustrating the interference between the light reflected by the substrate surface $1a$ of the reticle and the light directly impinging on the particle 10 and reflected thereby. Now, a case where reflection light is to be received in a direction perpendicular to the substrate surface $1a$ will be explained. As laser beams S1 and S2 are incident each with an incidence angle $\theta$ with respect to a normal to the reticle 1, the light beam S1 directly impinges on the particle 10 (point A) and is reflected thereby. Then, it advances perpendicularly toward the light receiving system. The light beam S2 is once reflected by the surface $1a$ (point B) of the reticle 1 substrate and then it impinges on the particle 10 (near point A), and finally it advances perpendicularly toward the light receiving system.

Considering the interference between these two lights S1 and S2, if the incidence angle $\theta$ with respect to a normal to the reticle 1 is about 89 deg., it can be approximated that the points of reflection of the lights S1 and S2 on the surface of the particle 10 are in common substantially at the same point A. The optical path difference d of the two lights S1 and S2 with reference to the point A is:

$$d = 2D'\cos\theta \quad (1)$$

wherein D' is the height of the point A from the surface $1a$ of the reticle substrate, and it can be determined by:

$$D = (D/2)(1+\cos\alpha)$$
$$\alpha = (\tfrac{1}{2})(\pi/2-\theta) \quad (2)$$

If the amplitude reflectance at the point B is $r_1$ and the amplitude reflectance at the point A is $r_2$, then the amplitude rS can be expressed by:

$$rS = r_2 S1 + r_1 r_2 S2 \quad (3)$$

The intensity I thereof is expressed by:

$$\begin{aligned} I &= |rS|^2 \quad (4) \\ &= |r_2|^2 \cdot |1 + r_1 e^{idk}|^2 \\ &= r_2^2(1 + r_1^2 + 2r_1 \cos d) \end{aligned}$$

wherein k is $$k = 2\pi/\lambda$$

For each polarization component, the amplitude reflectances $r_1$ and $r_2$ can be calculated as follows:

$$r_{1s} = (\cos\theta - n_g\cos\theta')/(\cos\theta + n_g\cos\theta') \quad (5)$$

$$r_{1p} = (n_g\cos\theta - \cos\theta')/(n_g\cos\theta + \cos\theta') \quad (6)$$

$$r_{2s} = (\cos\alpha - n_p\cos\alpha')/(\cos\alpha + n_p\cos\alpha') \quad (7)$$

$$r_{2p} = (n_p\cos\alpha - \cos\alpha')/(n_p\cos\alpha + \cos\alpha') \quad (8)$$

wherein $\theta'$ is the angle of refraction by the glass substrate surface $1a$ of the reticle, and $\alpha'$ is the angle of refraction by the surface of the particle 10.

FIG. 5 shows the strength reflectivity R at the surface of induction material (here, refractivity $n \pm 1.5$) as calculated on the basis of equations (5)–(8), where $R = r^2$ (r is the amplitude reflectance).

Figure 6:
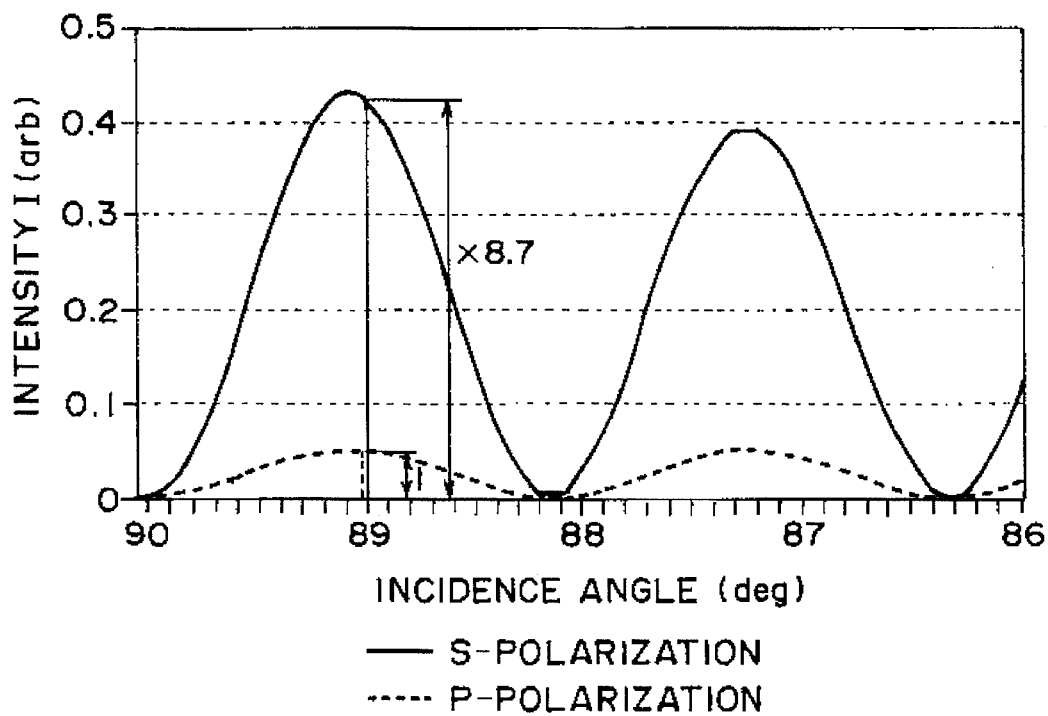
FIG. 6 is a graph for explaining changes in intensity of scattered light with variation in angle of incidence of light.

FIG. 6 shows the dependence of the intensity of reflected light, produced by a particle of 15 microns, upon the incidence angle, the results being obtained by calculation based on equations (5)–(8).

Since the amplitude reflectances $r_1$ and $r_2$ are different in the cases of P-polarized light and S-polarized light, there is produced a difference in intensity of scattered light between the case of S-polarized light and the case of P-polarized light such as shown in FIG. 5. If the incidence angle $\theta$ is close to 89 deg., between the S-polarized light and the P-polarized light there is a small difference in reflectivity at the point B on the substrate surface $1a$ of the reticle 1. On the other hand, at the point A on the particle 10 surface, the difference in reflectivity between the S-polarized light and the P-polarized light is large. Thus, as a result of the difference in reflectivity at the point A on the particle 10 surface, there is produced a difference in the change of scattered light intensity as depicted in FIG. 6.

Figure 7:
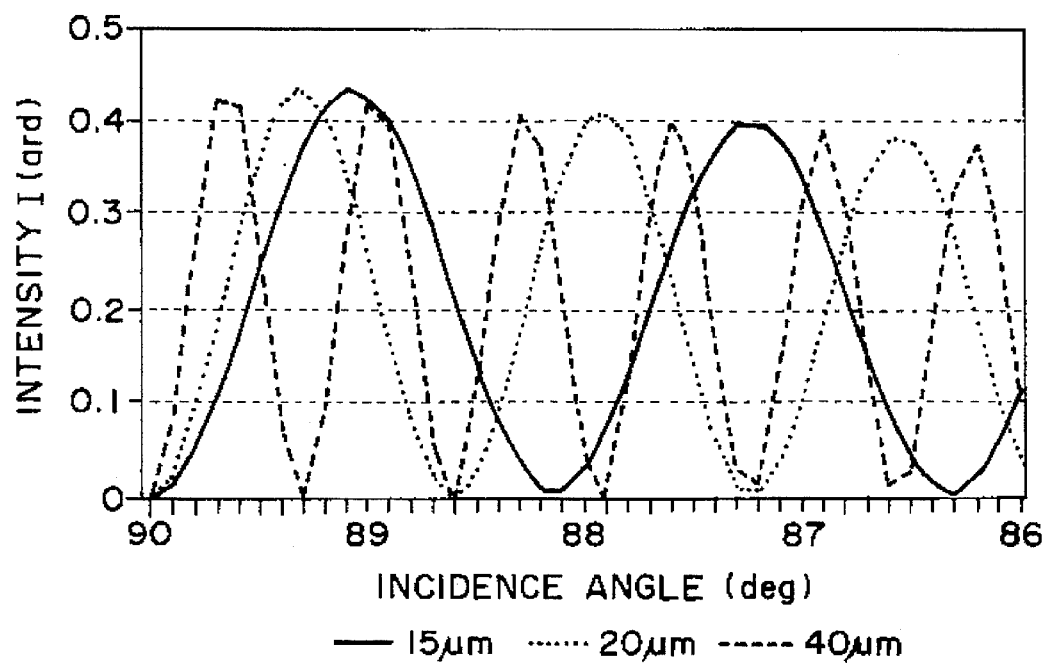
FIG. 7 is a graph wherein changes in intensity of scattered light with a variation in angle of incidence of light are plotted with respect to each of different particle sizes.

FIG. 7 shows the results of calculation of the intensity of scattered light varying with the incidence angle, the results being plotted with respect to difference sizes of particles. As seen from equations (2) and (4) mentioned above, the incidence angle and the particle size are parameters which determine the intensity of scattered light. Thus, the variation period (interference period) of the scattered light intensity changes with the particle size. This leads to a possibility that, if the incidence condition of the laser beam of the device is fixed to a certain incidence angle, only a small setting error of the incidence angle results in variation in scattered light intensity or that, in the light receiving system, a signal from a larger particle becomes weaker than a signal from a smaller particle.

Figure 9:
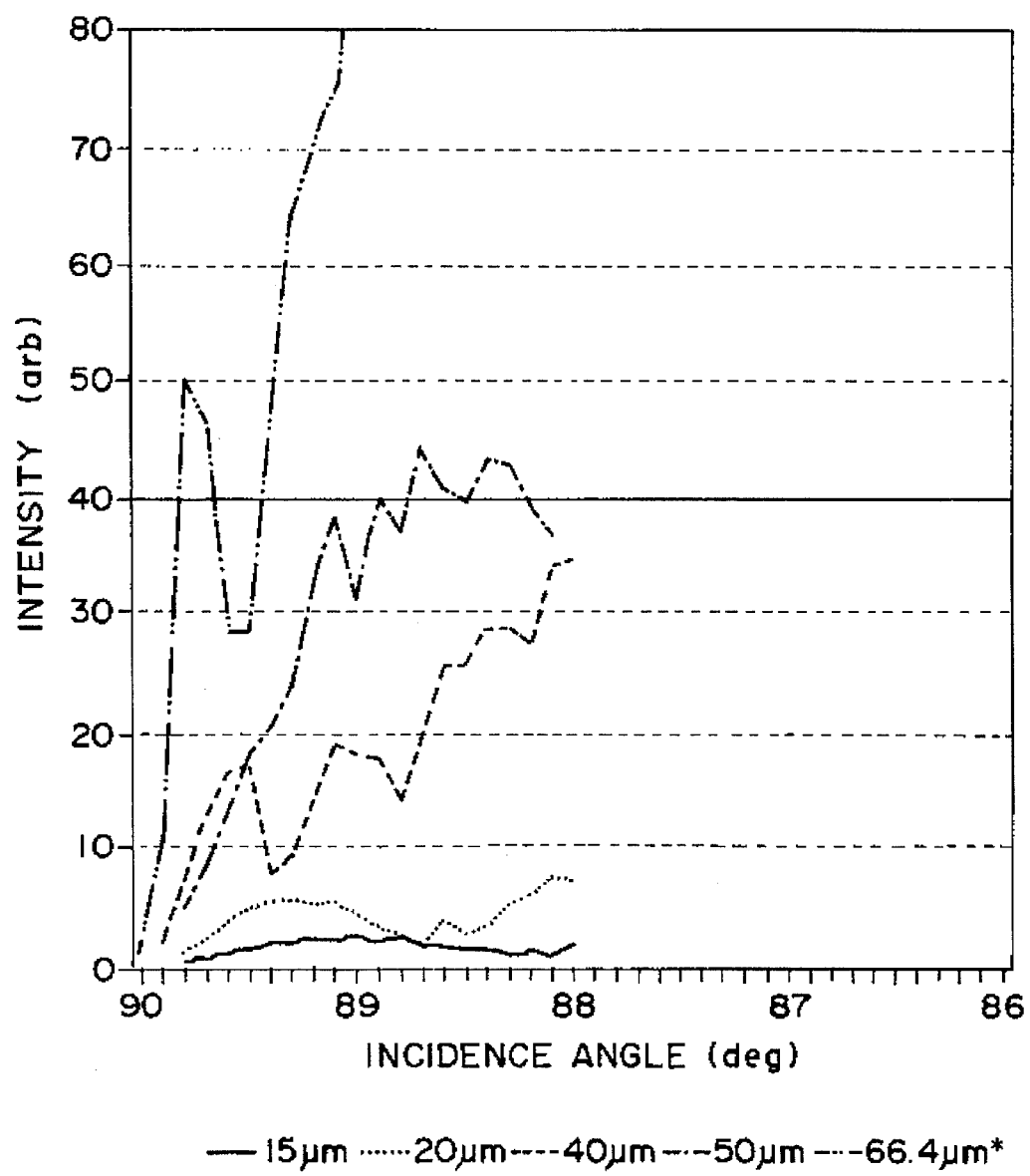
FIG. 9 is a graph wherein changes in intensity of scattered light with a variation in angle of incidence of light are plotted with respect to each of different particle sizes, where linearly polarized light being polarized in a direction substantially parallel to a plane containing the optical axis of illumination means and the optical axis of detecting means is inputted to the surface to be inspected.

FIGS. 8 and 9 show the results obtained by experimentally measuring the dependence of the intensity of scattered light from a polystyrene particle upon the incidence angle. FIG. 8 corresponds to a case where the direction of polarization of the light inputted to the substrate surface of the reticle 1 is in the S-polarization, while FIG. 9 corresponds to a case where the direction of polarization of the input light is placed parallel to a plane which is determined by the input light itself and the optical axis of the light receiving system. Noting particularly the interference period of scattered light intensity corresponding to each particle size in FIGS. 8 and 9, it is seen that the results qualitatively correspond to the results of simpler calculations made in relation to FIG. 7 with respect to the change in scattered light intensity (interference intensity) while taking the incidence angle and the particle size as the parameters. It is seen that in the latter case, since the intensity change due to the interference is smaller as compared with that in the former case, scattered light having an intensity surely dependent upon the particle size is obtainable.

Figure 10A:
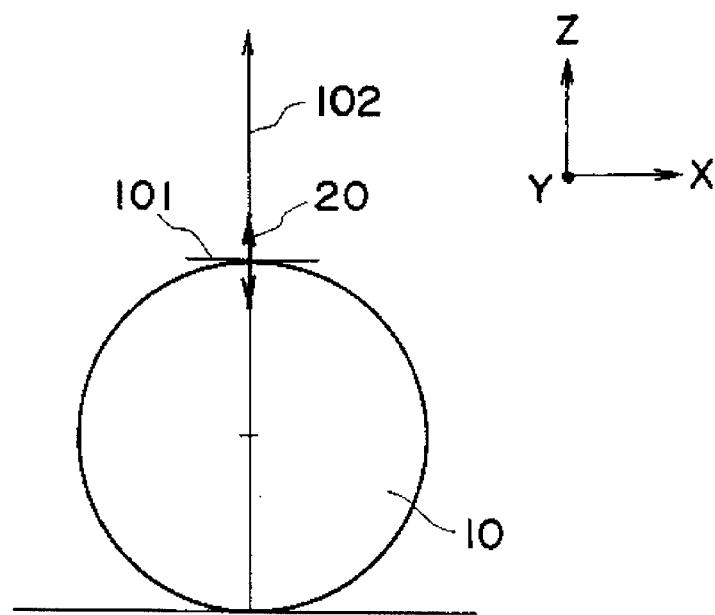
FIGS. 10A and 10B are schematic views for explaining the relation between the direction of polarization of input light and the light reception axis (optical axis of the optical system), wherein FIG. 10A corresponds to a case where the light reception axis is disposed along a direction of a normal to the surface to be inspected, and wherein FIG. 10B corresponds to a case where the light reception axis is disposed inclinedly with respect to the direction of a normal to the surface to be inspected.
Figure 10B:
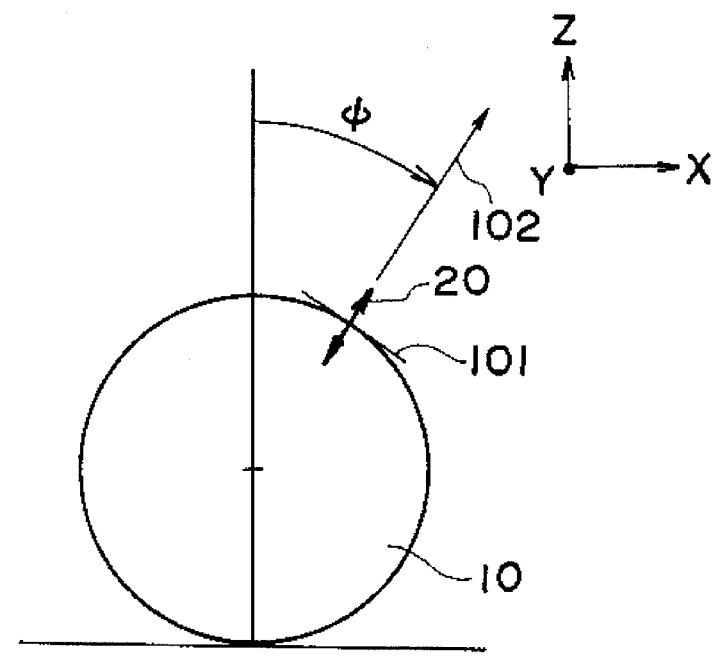

While the foregoing description has been made of an example wherein light is received in a direction perpendicular to the reticle 1, the light receiving optical axis may be inclined with respect to a normal to the reticle 1 so as to avoid reception by the sensor of unwanted noise from the circuit pattern bearing surface of the reticle 1, as the first embodiment of FIGS. 1 and 2. On that occasion, since the difference in reflectivity at the surface of the particle 10 is dominant in relation to the change in scattered light intensity, the polarization axis 20 (FIGS. 10A and 10B) of the input light may be set so as to be parallel to the plane determined by the optical axis of the input light and the light receiving optical axis 102, as shown in FIGS. 10A and 10B. If this is done, since the reflection at the surface 101 of the particle 10 is considered to be P-polarization, it is possible to reduce the change in intensity of scattered light due to the interference. Of these drawings, FIG. 10A corresponds to a case where the scattered light is to be received in the perpendicular direction, and FIG. 10B corresponds to a case where it is to be received in a direction inclined by the φ deg. with respect to the normal.

Figure 11:
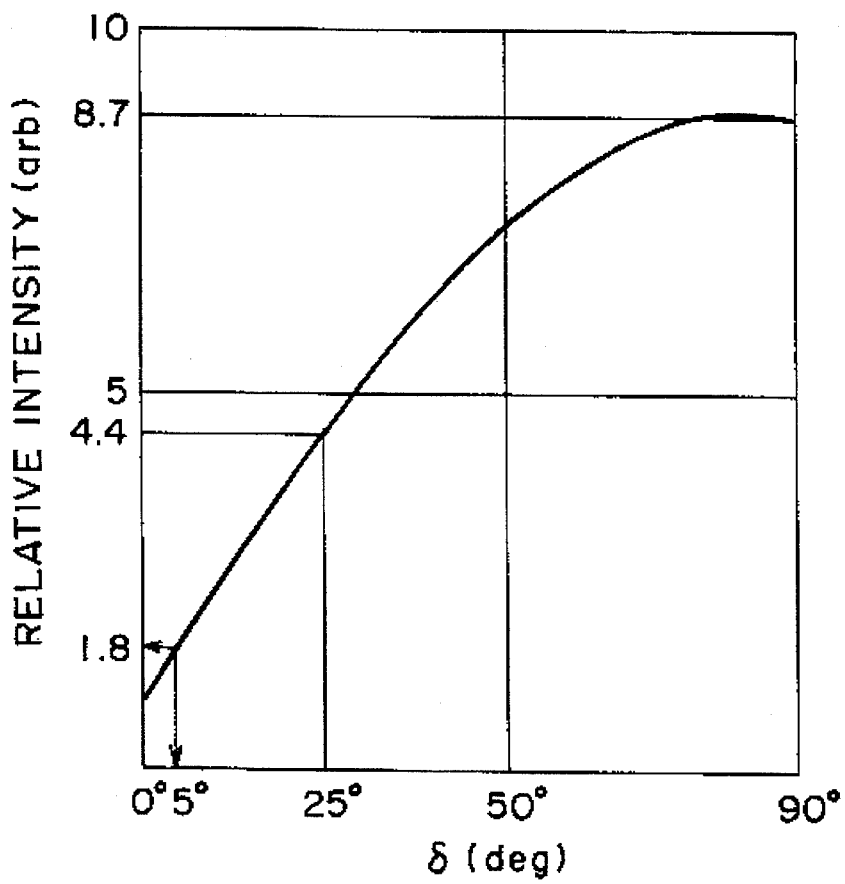
FIG. 11 is a schematic illustration for explaining a second embodiment of the present invention.
Figure 11:
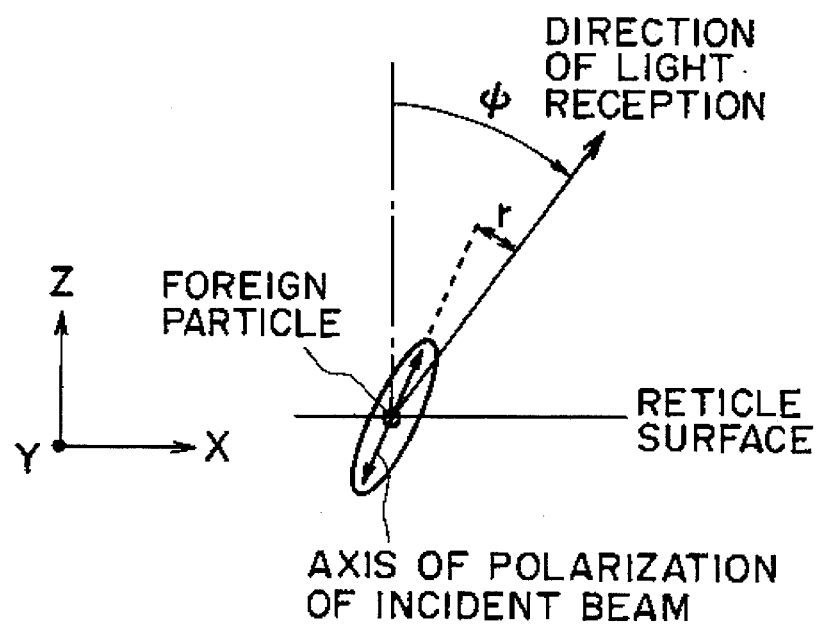

FIG. 11 shows the results of calculation of the relative intensity of varying output while taking, as "1", the intensity assumed at the time of r=0 (deg.) where r is the angle defined between the light receiving optical axis and the polarization axis of the input light. It is seen from this graph that, to reduce the output variation due to interference to ⅕ or less, the polarization axis of the input beam may be set at an angle of ±5 (deg.) with respect to the plane determined by the input light and the light receiving optical axis.

In the first embodiment of FIGS. 1 and 2, parallel light is projected to the surface 1a of the reticle 1 substrate. However, it is within the scope of the present invention that a convergent light is obliquely projected to the surface 1a of the reticle 1 substrate.

Figure 12:
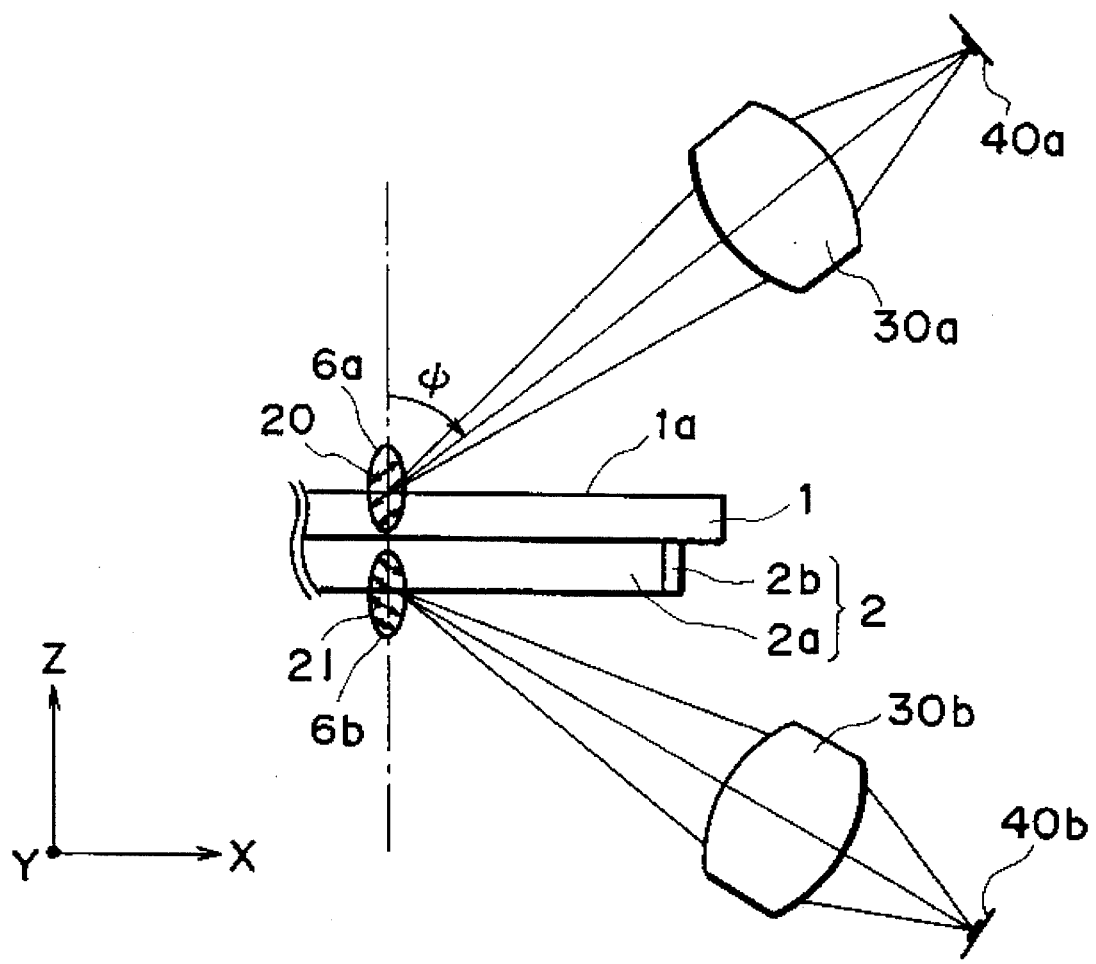
FIG. 12 is a schematic illustration for explaining a third embodiment of the present invention.

FIG. 12 is a schematic view of a second embodiment of the present invention. As compared with the first embodiment wherein a lens array is used as an imaging optical system, in the present embodiment ordinary imaging lenses 30a and 30b are used as the imaging optical system. The remaining structure of the second embodiment is essentially the same as that of the first embodiment, and also the second embodiment assures accurate particle inspection as in the first embodiment. Reference numerals 40a and 40b in the drawing denote sensor arrays.

FIGS. 13A and 13B are schematic views of a third embodiment of the present invention, wherein FIG. 13A is a sectional view and FIG. 13B is a plan view. Like numerals as of those of FIG. 14 are assigned to corresponding elements. As compared with the first embodiment wherein the sensor array is disposed at the imaging plane of the imaging optical system, in the third embodiment sensor arrays 40a and 40b each is provided at the position of an aperture stop which defines the pupil plane of the imaging lens 30a or 30b. The remaining structure of this embodiment is essentially the same as that of the first embodiment, and this embodiment assures accurate particle inspection as in the first embodiment.

FIGS. 14A and 14B are schematic views of a fourth embodiment, wherein FIG. 14A is a sectional view and FIG. 14B is a plan view. Like numerals as of those of FIG. 13 are assigned to corresponding elements. In the fourth embodiment, as compared with the first embodiment wherein the sensor array is disposed on the imaging plane of the imaging optical system, sensor arrays 40a and 40b each is provided at the location off the position of an aperture stop 41a or 41b which defines the pupil plane and the imaging plane of the imaging lens 30a or 30b. The remaining structure of the fourth embodiment is essentially the same as that of the first embodiment, and the fourth embodiment assures accurate particle inspection as in the first embodiment.

The surface inspection device having been described with reference to any one of the embodiments of FIGS. 1, 2 and 12–14 can be incorporated into (or used independently of) an exposure apparatus, for example, for manufacture of semiconductor memories, semiconductor microprocessors, magnetic heads, CCDs or liquid crystal panels, for example, in order to execute precise inspection of the state of a surface such as a reticle surface or mask surface, for example, on which a pattern for manufacture of any one of these microdevices are formed. If a surface inspection device is to be incorporated into an exposure apparatus, as an example it may be disposed in a portion of a reticle conveying path between a reticle changer and a reticle stage of the exposure apparatus.

Figure 15:
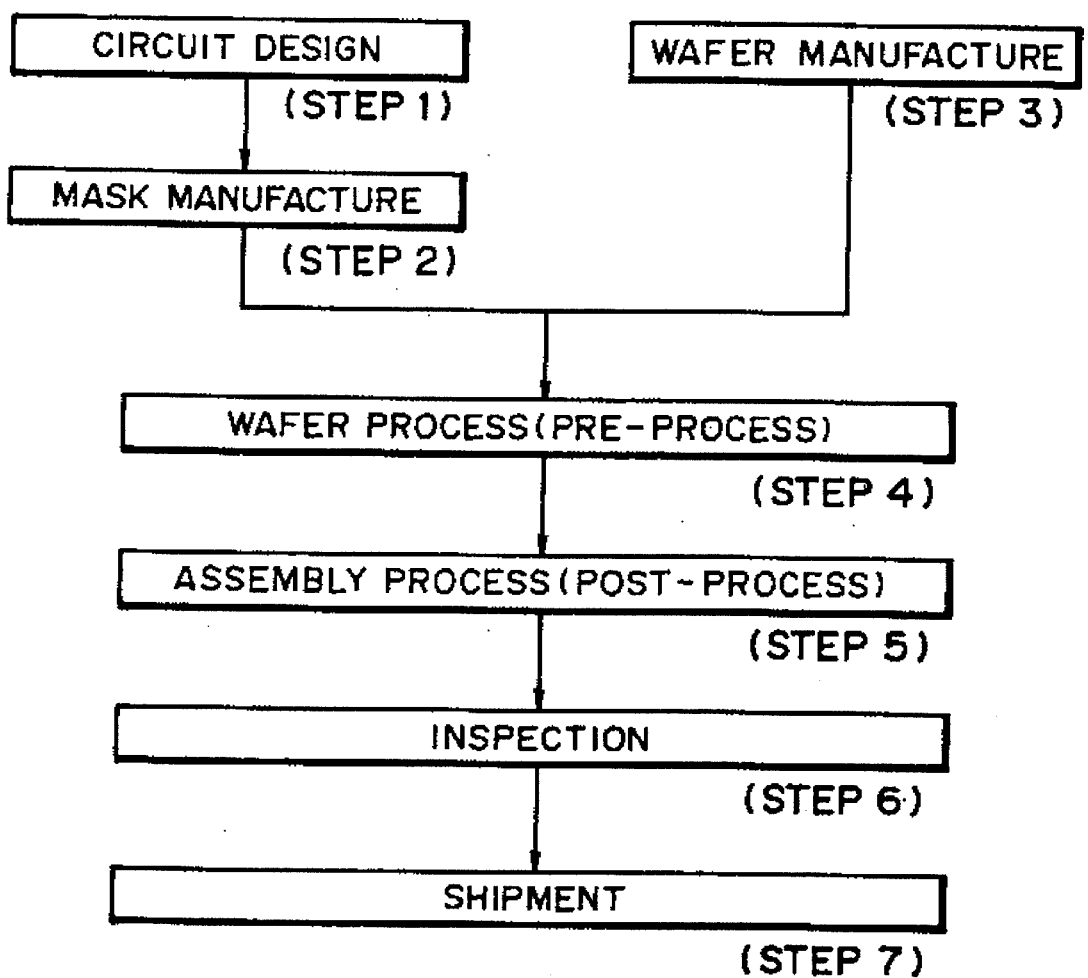
FIG. 15 is a flow chart of semiconductor device manufacturing processes.

Now, an embodiment of a semiconductor device manufacturing method based on an exposure apparatus such as described, will be explained. FIG. 15 is a flow chart of the sequence of manufacturing a semiconductor device such as a semiconductor chip (e.g. IC or LSI), a liquid crystal panel or a CCD, for example. Step 1 is a design process for designing the circuit of a semiconductor device. Step 2 is a process for manufacturing a mask on the basis of the circuit pattern design. Step 3 is a process for manufacturing a wafer by using a material such as silicon.

Step 4 is a wafer process which is called a pre-process wherein, by using the so prepared mask and wafer, circuits are practically formed on the wafer through lithography. Step 5 subsequent to this is an assembling step which is called a post-process wherein the wafer processed by step 4 is formed into semiconductor chips. This step includes assembling (dicing and bonding) and packaging (chip sealing). Step 6 is an inspection step wherein operability check, durability check and so on of the semiconductor devices produced by step 5 are carried out. With these processes, semiconductor devices are finished and they are shipped (step 7).

Figure 16:
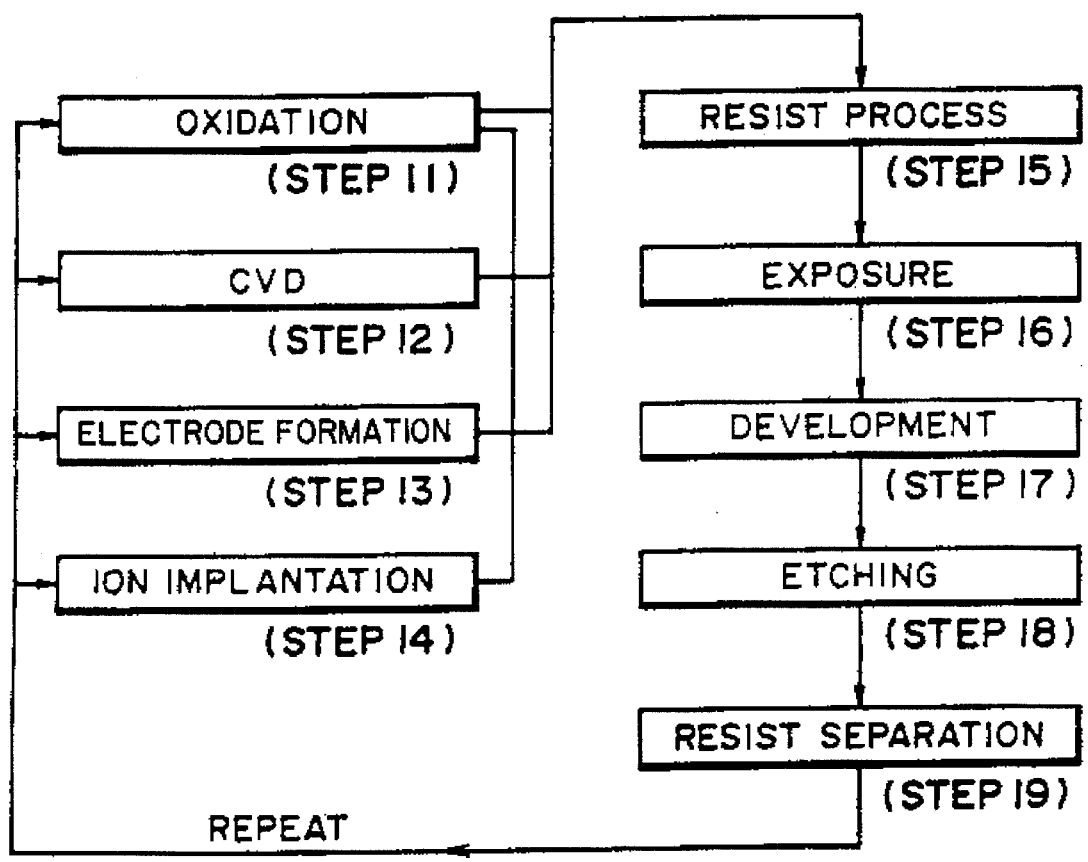
FIG. 16 is a flow chart of a wafer process.

FIG. 16 is a flow chart showing details of the wafer process. Step 11 is an oxidation process for oxidizing the surface of a wafer. Step 12 is a CVD process for forming an insulating film on the wafer surface. Step 13 is an electrode forming process for forming electrodes on the wafer by vapor deposition. Step 14 is an ion implanting process for implanting ions to the wafer. Step 15 is a resist process for applying a resist (photosensitive material) to the wafer. Step 16 is an exposure process for printing, by exposure, the circuit pattern of the mask on the wafer through the exposure apparatus described above. Step 17 is a developing process for developing the exposed wafer. Step 18 is an etching process for removing portions other than the developed resist image. Step 19 is a resist separation process for separating the resist material remaining on the wafer after being subjected to the etching process. By repeating these processes, circuit patterns are superposedly formed on the wafer.

While the invention has been described with reference to the structures disclosed herein, it is not confined to the details set forth and this application is intended to cover such modifications or changes as may come within the purposes of the improvements or the scope of the following claims.

What is claimed is:

1. An inspection device for inspecting for particles on a surface of a substrate, said apparatus comprising:

illumination means for projecting a light beam to the surface of the substrate, said illumination means having a light projection axis oriented at a small angle relative to the surface of the substrate so that said illumination means defines a linear illumination region on the surface of the substrate; and detecting means for detecting scattered light from the surface of the substrate in the linear illumination region to determine the size of particles in the linear illumination region, said detecting means having a light receiving axis inclined with respect to a normal to the substrate, wherein the projected light beam comprises linearly polarized light, being polarized in a direction substantially parallel to a plane which contains the light projection axis and the light receiving axis.

2. A device according to claim 1, wherein the optical axis of said illumination means defines an angle of 3.5±3 degrees with respect to the surface.

3. A device according to claim 1, further comprising moving means for moving said illumination means and said detecting means as a unit in a direction perpendicular to the optical axis of said detecting means and parallel to the surface.

4. A device according to claim 1, wherein the light beam comprises parallel light.

5. A device according to claim 1, wherein the light beam comprises convergent light.

6. A device according to claim 1, wherein said detecting means comprises an imaging optical system for imaging the surface.

7. A device according to claim 6, wherein said imaging optical system comprises a lens array comprising arrayed lens elements.

8. A device according to claim 6, wherein said detecting means comprises a sensor array disposed at the imaging position of said imaging optical system.

9. An exposure apparatus, comprising:

illumination means for projecting a light beam onto a surface of a mask, to be inspected, said mask having a pattern to be exposed, said illumination means having a light projection axis oriented at a small angle relative to the surface of the mask so that said illumination means defines a linear illumination region on the surface of the mask; and detecting means for detecting scattered light from the surface of the mask in the linear illumination region to determine the size of particles in the linear illumination region, said detecting means having a light receiving axis inclined with respect to a normal to the mask, wherein the projected light beam comprises linearly polarized light, being polarized in a direction substantially parallel to a plane which contains the light projection axis and the light receiving axis.

10. An apparatus according to claim 9, wherein the optical axis of said illumination means defines an angle of 3.5±3 degrees with respect to the surface.

11. An apparatus according to claim 9, wherein the surface to be inspected comprises a patterned surface on which the pattern is formed.

12. An apparatus according to claim 9, wherein the surface to be inspected comprises a surface of a pellicle protection film of the mask.

13. A device manufacturing method, comprising the steps of:

projecting, using illumination means, a light beam onto a surface of a mask to be inspected, the mask having a pattern to be exposed, the illumination means having a light projection axis oriented at a small angle relative to the surface of the mask so that the illumination means defines a linear illumination region the surface of the mask;

detecting scattered light from the surface of the mask in the linear illumination region to determine the size of particles in the linear illumination region using detecting means having a light receiving axis inclined with respect to a normal to the mask, wherein the projected light beam comprises linearly polarized light, being polarized in a direction substantially parallel to a plane which contains the light projection axis and the light receiving axis; and transferring by exposure the pattern of the mask, having been inspected on the basis of the detection of scattered light, to a wafer.

14. A method according to claim 13, wherein the projected light beam defines an angle of 3.5±3 degrees with respect to the surface to be inspected.

15. A method according to claim 13, wherein the surface comprises a patterned surface on which the pattern is formed.

16. A method according to claim 13, wherein the surface comprises a surface of a pellicle protection film of the mask.

* * * * *

UNITED STATES PATENT AND TRADEMARK OFFICE
CERTIFICATE OF CORRECTION

PATENT NO. : 5,585,916
DATED : December 17, 1996
INVENTOR(S) : Seiya MIURA, et al.

It is certified that error appears in the above-indentified patent and that said Letters Patent is hereby corrected as shown below:

COLUMN 1:

Line 19, "if" should read --If--.

COLUMN 6:

Line 21, "difference" should read --different--.

COLUMN 10:

Line 15, "region the" should read --region on the--.

Signed and Sealed this

Tenth Day of June, 1997

Attest:

BRUCE LEHMAN

*Attesting Officer*    Commissioner of Patents and Trademarks